United States Patent [19]

Ito et al.

[11] Patent Number: 4,968,609

[45] Date of Patent: Nov. 6, 1990

[54] CORYNEFORM BACTERIA CARRYING RECOMBINANT DNA AND A PROCESS FOR PRODUCING AROMATIC AMINO ACIDS USING SAID BACTERIA

[75] Inventors: Hisao Ito, Kawasaki; Katsuaki Sato, Yokosuka; Kazuhiko Matsui, Kawasaki; Konosuke Sano, Tokyo; Shigeru Nakamori; Takashi Tanaka, both of Yokohama; Hitoshi Enei, Zushi, all of Japan

[73] Assignee: Ajinomoto Co., Inc., Tokyo, Japan

[21] Appl. No.: 316,961

[22] Filed: Feb. 28, 1989

Related U.S. Application Data

[63] Continuation-in-part of Ser. No. 800,165, Nov. 20, 1985, abandoned.

[30] Foreign Application Priority Data

Nov. 20, 1984 [JP] Japan .................................. 59-245700
Aug. 30, 1985 [JP] Japan .................................. 60-191523

[51] Int. Cl.$^5$ ........................ C12P 13/22; C12N 1/21; C12N 15/52; C12N 15/77
[52] U.S. Cl. .................................. 435/108; 435/69.1; 435/71.1; 435/170; 435/172.1; 435/172.3; 435/252.3; 435/252.32; 435/320; 435/840; 435/843; 935/9; 935/29; 935/60; 935/72

[58] Field of Search .................. 435/69.1, 71.1, 172.3, 435/252.32, 172.1, 108, 170, 320, 843, 840; 935/29, 6, 9, 10, 60, 72

[56] References Cited

U.S. PATENT DOCUMENTS 4,500,640 2/1985 Katsumata et al. ................. 435/253

FOREIGN PATENT DOCUMENTS 0077196 4/1983 European Pat. Off. .

OTHER PUBLICATIONS

Hagino et al. Agr. Biol. Chem. 38(11) 2125–2134 (1974).

Primary Examiner—Richard A. Schwartz
Assistant Examiner—Richard C. Peet
Attorney, Agent, or Firm—Oblon, Spivak, McClelland, Maier & Neustadt

[57] ABSTRACT

The present invention relates to a process for producing an aromatic amino acid which comprises culturing a Coryneform bacterium carrying a recombinant DNA constructed by connecting (1) a gene capable of being expressed in a Coryneform bacterial cell and coding for 3-deoxy-D-arabino-heptulonic acid-7-phosphate synthetase with (2) a plasmid vector capable of propagating in a Coryneform bacterial cell.

15 Claims, 2 Drawing Sheets

CORYNEFORM BACTERIA CARRYING RECOMBINANT DNA AND A PROCESS FOR PRODUCING AROMATIC AMINO ACIDS USING SAID BACTERIA

This is a continuation, of application Ser. No. 0/800,165, filed Nov. 20, 1985, now abandoned.

BACKGROUND OF THE INVENTION

The present invention relates to Coryneform bacteria carrying a recombinant DNA molecules having inserted therein a gene coding for 3-deoxy-D-arabinoheptulonic acid-7-phosphate synthetase (hereafter referred to as "DS") and to processes for producing aromatic amino acids utilizing such bacteria.

DS is an enzyme which catalyses the synthesis of 3-deoxy-D-arabino-heptulonic acid-7-phosphate (hereafter referred to as "DAHP") from phosphoenolpyruvic acid and erythrose-4-phosphate. DAHP is converted into phenylalanine, tyrosine or tryptophan via chorismic acid. With respect to Coryneform bacteria, it is known that DS activity is synergistically inhibited by phenylalanine and tyrosine, which are final products. When breeding aromatic-amino-acid-producing bacteria, it is important to select a strain having potent DS activity, i.e., free from inhibition.

On the other hand, some processes for breeding aromatic-amino-acid-producing bacteria by recombinant DNA techniques are known (for example, Published Unexamined Japanese Patent Application Nos. 208994/82, 71397/82, 89194/83, 134994/83, etc.). In these processes, however, genes coding for DS of Coryneform bacteria (hereafter referred to as "DS gene") have not been inserted.

SUMMARY OF THE INVENTION

The present invention relates to microorganisms having a high productivity of aromatic amino acids and a process for producing the aromatic amino acids using these microorganisms more efficiently.

We have succeeded in isolating Coryneform bacteria carrying a recombinant DNA constructed by connecting a gene, expressing in a Coryneform bacterial cell and coding for DS, with a plasmid vector capable of replicating in a Coryneform bacterial cell. We have found that the thus obtained Coryneform bacteria possess high productivity of aromatic amino acids.

DESCRIPTION OF THE PREFERRED EMBODIMENTS

Figure 1:
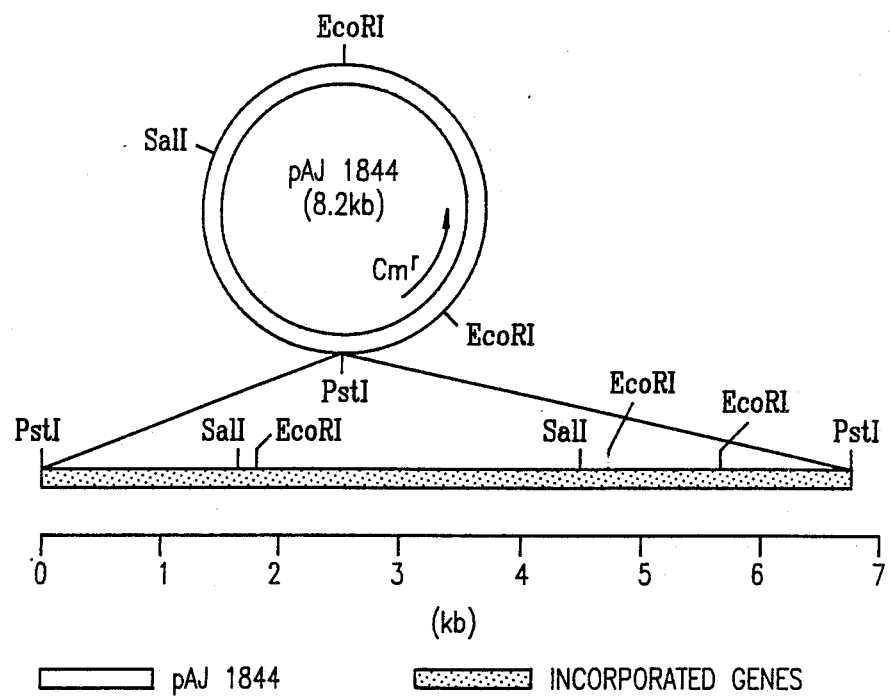
FIG. 1 is a restriction enzyme map of plasmid pAR-2.

Coryneform bacteria, as used in the present invention, are a series of microorganisms described in Bergey's Manual of Determinative Bacteriology, 8th edition, page 599 (1974) which are aerobic, grampositive, non-acid fast rods having no capability of forming spores. Among them, Coryneform bacterial producing glutamic acid, as described below, are most preferred.

Examples of wild strains of Coryneform glutamic acid-producing bacteria include the following:
*Brevibacterium divaricatum* ATCC 14020
*Brevibacterium saccarolyticum* ATCC 14066
*Brevibacterium lactofermentum* ATCC 13869
*Brevibacterium roseum* ATCC 13825
*Brevibacterium flavum* ATCC 13826
*Brevibacterium thiogenitalis* ATCC 19240
*Corynebacterium acetoacidophilum* ATCC 13870
*Corynebacterium acetoglutamicum* ATC 15806
*Corynebacterium callunae* ATCC 15991
*Corynebacterium glutamicum* ATCC 13032, 13060
*Corynebacterium lilium ATCC* 15990
*Corynebacterium melassecola* ATCC 17965
*Corynebacterium ammoniaphilum* ATCC 15354

In addition to the above-mentioned glutamic acid-producing Coryneform bacteria, the glutamic acid-producing Coryneform bacteria of the present invention include mutants which possess glutamic acid productivity or have lost glutamic acid productivity.

To isolate the DS genes, chromosomal genes are first extracted (for example, a method described in H. Saito and K. Miura, Biochem. Biophys. Acta, 72, 619 (1963) can be used) from strains which contain the DS genes and are then digested with an appropriate restriction enzyme. The chromosomal genes digested are then ligated with plasmid vectors capable of replicating in Coryneform bacteria. Using the resulting recombinant DNA, DS-deficient mutants of Coryneform bacteria are transformed and strains which come to possess DS activity are isolated. From these strains, the DS genes can be isolated.

Further it is also possible to transform the wild strains of Coryneform bacteria using similar recombinant DNA, to culture strains which have come to acquire resistance to antagonists of the aromatic amino acids (those having an inhibitory effect against the DS activity, etc.) and to isolate the DS genes using these strains.

Some examples of antagonists of the aromatic amino acids include o-fluorophenylalanine, m-fluorophenylalanine, p-fluorophenylalanine, p-aminophenylalanine, β-3-thienylalanine, 3-aminotyrosine, tyrosine hydroxamate, 5-methyltryptophan.

DNA donor bacteria are preferably mutants obtained by imparting a mutation, such as resistance to the aforesaid aromatic amino acid antagonists, or mutants in which the biosynthetic activity of the aromatic amino acid or its precursor is enhanced.

The precursor of an aromatic amino acid as used herein refers to DAHP, 3-dehydroquinic acid, 3-dehydroshikimic acid, shikimic acid, shikimic acid-3-phosphate, 5-enolpyruvylshikimic acid-3-phosphate, chorismic acid, prephenic acid, phenylpyruvic acid, anthranilic acid, indole-3-glycerol phosphate, etc.

Some examples of such mutants are described in U.S. Pat. Nos. 3,660,235, 3,759,970, Published Unexamined Japanese Patent Application 64793/81.

Wild strains or mutants can be used as a source of DS genes. A gene modified so as to code for DS having a reduced degree of synergistic inhibition of phenylalanine and tyrosine is particularly preferred when using mutant genes.

To obtain the mutant genes, DNA donor bacteria may be subjected to a mutation treatment; alternatively, after inserting the DS gene into a vector plasmid, the obtained recombinant DNA may be introduced into a DNA recipient and the thus obtained transformant subjected to a mutation treatment. The mutant gene may also be obtained by subjecting the above-described recombinant DNA per se to a mutation treatment in vitro.

A wide variety of restriction enzymes can be employed to cleave the chromosomal genes, if the degree of cleavage can be controlled, for example, by controlling the time for the cleavage reaction. The plasmid vector used in the present invention can be any vector as long as it can be replicated in cells of Coryneform bacteria. Specific examples include the following:

(1) pAM 330 cf. Published Unexamined Japanese Patent Application 67699/83
(2) pHM 1519 cf. Published Unexamined Japanese Patent Application 77895/83
(3) pAJ 655 Published Unexamined Japanese Patent Application 216199/83
(4) pAJ 611 same as above
(5) pAJ 1844 same as above
(6) pCG 1 cf. Published Unexamined Japanese Patent Application 134500/82
(7) pCG 2 cf. Published Unexamined Japanese Patent Application 35197/83
(8) pCG 4 cf. Published Unexamined Japanese Patent Application 183799/82
(9) pCG 11 same as above The plasmid vector DNA is cleaved by the same restriction enzyme as the chromosomal DNA, which may cleave one portion of the DNA or alternatively may partially cleave a plurality of portions.

The vector DNA is cleaved by the same restriction enzyme used for cleavage of the chromosomal gene, or the vector DNA is connected with an oligonucleotide having a complementary base sequence at its respective terminals for the chromosomal DNA cleavage fragment and the cleaved vector DNA. Then, the resulting composite is subjected to a ligation reaction to join the plasmid vector and the chromosomal fragment.

The incorporation of the thus obtained recombinant DNA of the chromosomal DNA and the vector plasmid into recipients belonging to Coryneform bacteria can be done by a method which comprises treating the recipient cells with calcium chloride to increase the permeability of DNA, as is reported regarding *Escherichia coli* K-12 (Mandel, M. and Higa, A., *J. Mol. Biol.*, 53, 159 (1970). A method which comprises incorporating the recombinant DNA at a stage of growth (the so-called competent cell) when cells become capable of incorporating DNA, is reported for *Bacillus subtilis* (Duncan, C. H., Wilson, G. A. and Young, F. E., Gene, 1, 153 (1977)). Alternatively, it is also possible to incorporate the plasmids into the DNA recipients by forming protoplasts or spheroplasts of the DNA recipients which easily incorporate plasmid DNA, as is known for *Bacillus subtilis*, *Actinomycetes* and yeast (Chang, S. and Cohen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. U.S.A.*, 75, 1929 (1978)).

In the protoplast technique, sufficiently high frequency can be obtained even by the above-described process used for *Bacillus subtilis* and by a process which comprises allowing DNAs to incorporate into protoplasts of the genus Corynebacterium or the genus Brevibacterium, described in Published Unexamined Japanese Patent Application 183799/82, in the presence of polyethylene glycol or polyvinyl alcohol and divalent metal ions. Similar results can also be obtained by a process in which the incorporation of DNA is accelerated by the addition of carboxymethyl cellulose, dextran, phycoll, Pluronic F 68 (Serva Co., Ltd.), etc. in place of polyethylene glycol or polyvinyl alcohol.

Transformants obtained using wild strains or DS-deficient strains as hosts may be employed as the aromatic-amino-acid-producing bacteria but the use of specific hosts as shown below often provides strains having a high productivity of the aromatic amino acids.

For the production of tyrosine, some examples are (i) mutants belonging to the genus Corynebacterium which require phenylalanine and have resistance to 3-aminotyrosine, p-aminophenylalanine, p-fluorophenylalanine or tyrosine hydroxamate as described in H. Hagino, K. Nakayama: Agric. Biol. Chem., 37, 2013 (1973); and (ii) mutants belonging to the genus Brevibacterium which are resistant to m-fluorophenylalanine as described in Sugimoto, Nakagawa, Tsuchida and Shiio, Agric. Biol. Chem., 37, 2327 (1973).

For the production of tryptophan, examples include (i) mutants belonging to the genus Brevibacterium which require phenylalanine and tyrosine and are resistant to 5-methyltryptophan (I. Shiio, H. Sato, M. Nakagawa, Agric. Biol. Chem., 36, 2315 (1972)), (ii) mutants belonging to the genus Brevibacterium which require phenylalanine and are resistant to m-fluorophenylalanine or 5-fluorotryptophan (I. Shiio, S. Sugimito, M. Nakagawa, Agric. Biol. Chem., 39, 627 (1975)), (iii) mutants belonging to the genus Brevibacterium which require tyrosine and are resistant to 5-fluorotryptophan or azaserine; and (iv) mutants belonging to the genus Corynebacterium which require phenylalanine or tyrosine and are resistant to 5-methyltryptophan, 4-methyltryptophan, 6-fluorotryptophan, tryptophan hydroxamate, p-fluorophenylalanine, tyrosine hydroxamate or phenylalanine hydroxamate (H. Hagino, K. Nakayama, Agric. Biol. Chem., 39, 345 (1975)).

For the production of phenylalanine, examples include (i) mutants belonging to the genus Brevibacterium which have resistance to m-fluorophenylalanine (S. Sugimoto, M. Nakagawa, T. Tsuchida, I. Shiio, Agric. Biol. Chem., 37, 2327 (1973)), (ii) mutants belonging to the genus Brevibacterium which require tyrosine or methionine and have resistance to 5-methyltryptophan or p-fluorophenylalanine (Published Unexamined Japanese Patent Application 116294/74); (iii) mutants belonging to the genus Brevibacterium which require tyrosine or methionine, have resistance to 5-methyltryptophan or p-fluorophenylalanine and have sensitivity to decoinine (Published Unexamined Japanese Patent Application 64793/81); and (iv) mutants belonging to the genus Corynebacterium which require tyrosine and have resistance to p-fluorophenylalanine or p-aminophenylalanine (H. Hagino, K. Nakayama, Agric. Biol. Chem., 38, 157 (1974)).

When other genes are incorporated into the host cell in addition to the DS gene, the productivity of the aromatic amino acids is often enhanced.

Examples of such genes include 3-dehydroquinic acid gene, 3-dehydroquinic acid dehydratase gene, shikimic acid dehydrogenase gene, shikimic acid kinase gene, 5-enolpyruvyl shikimic acid-3-phosphate synthetase gene, chorismic acid synthetase gene, etc.

When tryptophan-producing bacteria are desired the incorporation of anthranilic acid synthetase gene, anthranilic acid phosphoribosyl transferase gene, N-(5'-phosphoribosyl)anthranilic acid isomerase gene, indole-3-glycerol phosphate synthetase gene, tryptophan synthetase gene, etc. sometimes produces better results.

Further, when phenylalanine or tyrosine-producing bacteria are wanted, it is desirable to incorporate prephenic acid dehydratase gene, prephenic acid transaminase gene, pretyrosine dehydrogenase gene, tyrosine aminotransferase gene, etc., in addition to the DS gene.

The production and accumulation of aromatic amino acids is accomplished by culturing the thus obtained Coryneform bacteria which are capable of producing the aromatic amino acids. Ordinary media containing carbon sources, nitrogen sources, inorganic ions and if necessary, further containing organic trace nutrients such as amino acids, vitamins, etc. are employed. As carbon sources, glucose, sucrose, lactose, etc. or starch hydrolysate solution containing these sugars, whey, molasses, etc. are employed. As nitrogen sources, ammonia gas, ammonia water, ammonium salts and others can be employed.

Cultivation is carried out under aerobic conditions while appropriately controlling the pH and the temperature of the medium until the production and accumulation of the aromatic amino acids are substantially discontinued.

EXAMPLE 1

(1) Preparation of chromosomal DNA containing the DS gene:

As a source of chromosomal DNA, the phenylalanineproducing bacteria, *Brevibacterium lactofermentum* AJ 11957 (FERM-P 6673), which came to possess resistance to m-fluorophenylalanine, a phenylalanine analog, was used. M-Fluorophenylalanine acts by releasing inhibition of DS due to phenylalanine.

The bacteria was inoculated on CMG medium (which contained 1 g/dl of peptone, 1 g/dl of yeast extract, 0.5 g/dl of glucose and 0.5 g/dl of NaCl and had been adjusted to pH of 7.2). A shake culture was conducted at 30° C for about 3 hours and cells were harvested at an exponential growth phase.

After the cells were lysed by lysozyme and SDS, chromosomal DNA was extracted and purified by the conventional phenol method to finally obtain 3.5 mg of DNAs.

(2) Preparation of vector DNA:

The plasmid vector, pAJ 1844 (molecular weight, 5.4 megadaltons) was used and its DNA was prepared as follows.

First, *Brevibacterium lactofermentum* AJ 12037 (FERM BP-577) was inoculated on 100 ml of CMG medium. After culturing at 30° C to reach a late exponential growth phase, the cells were lysed by lysozyme and SDS. The supernatant was obtained by ultracentrifugation at 30,000×g for 30 minutes. After the treatment with phenol, 2 volumes of ethanol were added to recover the DNA as a precipitates. After the DNA was dissolved in a small quantity of TEN buffer (20 mM tris hydrochloride, 20 mM NaCl, 1 mM EDTA (pH 8.0)), the solution was subjected to agarose gel electrophoresis to separate the DNA fractions. The separated product was then excised to obtain about 15 Vg of pAJ 1844 plasmid DNAs.

(3) Incorporation of the vector into the chromosomal DNA fragment:

The chromosomal DNA, 10 obtained in (1), and 5 μg of the plasmid DNA obtained in (2) were treated with restriction endonuclease Pst I at 37° C. for 1 hour, respectively, to affect cleavage. After heat treatment at 65° C. for 10 minutes, the reaction solutions were mixed with each other and the mixture was subjected to a ligation reaction of the DNA strands with T4 DNA ligase at 10° C. for 24 hours in the presence of ATP and dithiothreitol. After heat treatment at 65° C. for 10 minutes, a 2-fold volume of ethanol was added to the reaction solution to precipitate and harvest the ligated DNA precipitates.

(4) Cloning of DS gene:

*Brevibacterium lactofermentum* AJ 12036 (FERM-P 7559) sensitive to m-fluorophenylalanine, was used as recipient.

A protoplast transformation method was used as the transformation method. First, the cells were cultured in 5 ml of CMG liquid medium to reach an early exponential growth phase. After adding 0.6 unit/ml of penicillin, a shake culture was conducted for an additional 1.5 hours. Cells were harvested by centrifugation and washed with 0.5 ml of SMMP medium (pH 6.5) composed of 0.5M sucrose, 20 mM maleic acid, 20 mM magnesium chloride and 3.5% Pennassay broth (Difco) and then suspended in SMMP medium containing 10 mg/ml of lysozyme. The suspension was treated at 30° C for 20 hours to obtain protoplasts. After centrifuging at 6000×g for 10 minutes, the protoplasts were washed with SMMP and resuspended in 0.5 ml of SMMP. The thus obtained protoplasts were mixed with 10 μg of the DNA prepared in (3) in the presence of 5 mM EDTA. After polyethylene glycol was added to the mixture to reach a final concentration of 30%, the mixture was allowed to stand at room temperature for 2 minutes to incorporate DNA into the protoplasts. After the protoplasts were washed with 1 ml of SMMP medium, the protoplasts were resuspended in 1 ml of SMMP and, the suspension was cultured at 30° C. for 2 hours for phenotypic expression. The culture solution was spread onto a protoplast regeneration medium of pH 7.0. The regeneration medium contained, per one liter of distilled water, 12 g of tris(hydroxymethyl)aminomethane, 0.5 g of KCl, 10 g of glucose, 8.1 g of MgCl$_2$·6H$_2$O, 2.2 g of CaCl$_2$·2H$_2$O, 4 g of peptone, 4 g of yeast extract powder, 1 g of Casamino Acid (Difco Co., Ltd., Ltd.), 0.2 g of K$_2$HPO$_4$, 135 g of sodium succinate 8 g of agar and 3 μg/ml of chloramphenicol.

After culturing at 30° C. for 2 weeks, about 25000 colonies resistant to chloramphenicol appeared, which were replicated in minimal medium (which contained 2% of glucose, 1% of ammonium sulfate, 0.3% of urea, 0.1% of KH$_2$PO$_4$, 0.04% of MgSO$_4$·7H$_2$O, 2 ppm of iron ions, 2 ppm of manganese ions, 200 g/dl of thiamine hydrochloride, 50 μg/ml of biotin, 500 μg/ml of m-fluorophenylalanine and 10 μg/ml of chloramphenicol, pH 7.0, 1.8% of agar) to obtain 5 strains resistant to chloramphenicol and m-fluorophenylalanine.

(5) Analysis of transformant on plasmid:

From these strains, a lysate was prepared by the method described in (2). When plasmid DNA was detected by agarose gel electrophoresis, a plasmid obviously larger than vector pAJ 1844 was detected in all of the strains.

The plasmids of the 5 strains were cleaved with the restriction enzyme Pst I used for recombination. Among them, DNA incorporated fragments of 6.7 kb common to 4 strains were recognized.

Further in the remaining strain, 9 DNA-incorporated fragments of 3.7 kb, 3.0 kb, 1.7 kb, 1.6 kb, 1.4 kb, 1.3 kb, 0.8 kb, 0.7 kb and 0.4 kb were recognized. The portion of vector pAJ 1844 cleaved with Pst I was named pAR-2 in the former recombinant plasmid carrying the Pst I fragment of 6.7 kb and, the latter recombinant plasmid carrying 9 Pst I DNA fragments was named pAR-1. The strain carrying pAR-1 was named AJ 12181 (FERM-P 7948) and the strain carrying pAR-2 was named AJ 12182 (FERM-P 7947). pAR-2 has a restriction enzyme map shown in FIG. 1.

(6) Retransformation:

In order to confirm that the gene was present on the recombinant plasmid carrying the DNA fragment, Brev-ibacterium lactofermentum AJ 12036 was again transformed using the plasmids pAR1 and pAR-2.

Among the colonies which had chloramphenicolresistance, 50 strains were picked up and tested with respect to sensitivity to m-fluorophenylalanine. All of the strains demonstrated m-fluorophenylalanine resistance. Clearly the genes imparting the m-fluorophenylalanine resistance were present on the above-described plasmids.

(7) DS Activity of transformant:

The specimen strain was cultured at 30° C. for 15 hours in 20 ml of aromatic amino acid producing medium (which contained 130 g of glucose, 10 g of ammonium sulfate, 1 g/dl of $KH_2PO_4$, 1 g of $MgSO_4 \cdot 7H_2$, 12 gl of fumaric acid, 3 ml of acetic acid, 50 ml of soybean protein acid hydrolysate "Aji-Eki", 10 mg of $FeSO_4 \cdot 7H_2O$, 10 mg of $MnSO.4H_2O$, 50 μg of biotin, 2000 μg of thiamine hydrochloride and 50 μg of $CaCO_3$ in 1 liter of water; pH 7.0). From the obtained cells, a lysate solution was prepared by ultrasonic wave treatment and centrifuged at 32000×g for 20 minutes to obtain the supernatant. Using the supernatant as a crude enzyme solution, a reaction was carried out at 30° C. for 10 minutes in 1.0 ml of a reaction solution containing 50 mM tris-hydrochloride buffer (pH 7.5), 0.5 mM phosphoenolpyruvic acid and 0.5 mM erythrose-4-phosphate. After completion of the reaction, 0.2 ml of trichloroacetic acid was added to inactivate the enzyme. After the denatured proteins were removed by centrifugation, 0.025 mM of periodic acid was added to 0.25 ml of the obtained supernatant followed by incubation at 37° C. for 30 minutes. Thereto was added 0.5 ml of 2% sodium arsenite to discontinue the oxidation reaction Thereafter, 2.0 ml of 0.3% 2-thiobarbituric acid were added and the mixture was heated at 100° C. for 8 minutes. The absorbancy of the reaction solution at 549 nm was measured and the enzyme activity was determined using a molecular extinction coefficient for DAHP of $4.5 \times 10^4$ (Jensen, R. A. and Nester, E. W., J. Biol. Chem., 241, 3365 (1966)). The activity was also measured when either phenylalanine or tyrosine, or both were added to the reaction solution in an amount of 1 mM each and expressed by % when the activity was made 100% in the case of adding none. These results are shown in Table 1.

By incorporating the obtained recombinant plasmid, the DS activity increased by 2.6 to 14 times. The inhibitory pattern of activity with each amino acid was changed from the wild strain type to the mutant type, and it is evident that the m-fluorophenylalanine resistant gene coded for by pAR-1 and pAR-2 was the DS gene. Further, the Pst I fragment possessed by pAR-1 is quite different from that possessed by pAR-2 and it is thus believed that two or more genes coding for proteins having the DS activity are present

TABLE 1

| Strain | DS Activity | Residual Activity When Each Amino Acid Was Added | | |
|---|---|---|---|---|
| | | Tyrosine | Phenylalanine | Phenylalanine + Tyrosine |
| Brevibacterium lactofermentum AJ 11957 | 85.5 nmol/mg | 108 | 107 | 106 |
| Brevibacterium lactofermentum AJ 12036 | 13.7 | 51 | 94 | 23 |
| Brevibacterium lactofermentum AJ 12181 (AJ 12036/pAR-1) | 198 | 109 | 112 | 111 |
| Brevibacterium lactofermentum AJ 12182 (AJ 12036/pAR-2) | 35.4 | 88 | 99 | 82 |

(8) Subcloning of DS gene pAR-1 was cleaved with restriction enzyme Pst I. After heating at 65° C for 10 minutes, the system was subjected to ligation of the ENA strand with T4 DNA ligase by allowing it to stand overnight at 4° C. Then, the reaction solution was heated at 65° C. for 10 minutes and a 2-fold volume of ethanol was added to the reaction solution to collect the ligated DNA precipitates. A small amount of TEN buffer was added to the precipitates, which were then used for transformation.

Figure 2:
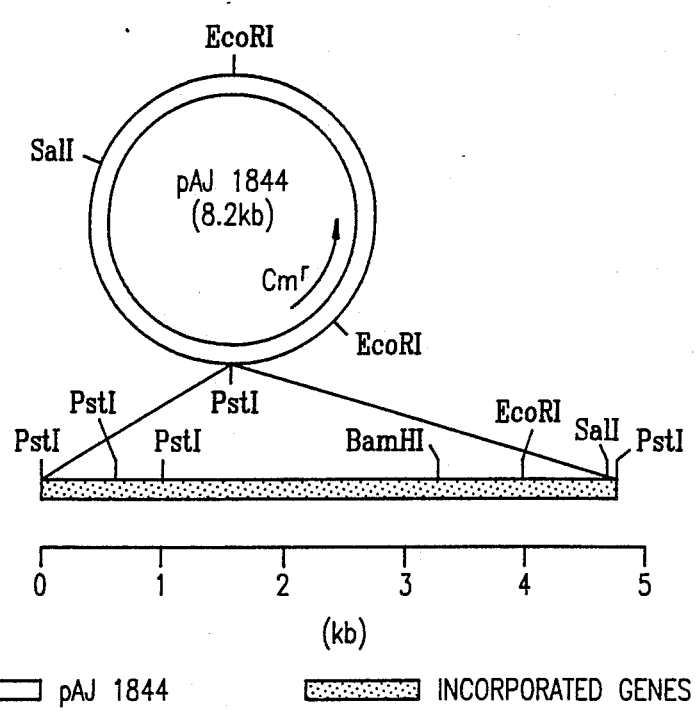
FIG. 2 is a restriction enzyme map of plasmid pAR-112. In the Figures, ▭ indicates pAJ 1844; ▬ indicates incorporated genes; and E, P, S and B indicate EcoRI, PSt I, Sal I and Bam HI, respectively.

Brevibacterium lactofermentum AJ 12036 was transformed using the transformation method described in (4). After regenerating at 30° C. for 2 weeks in regeneration medium containing 3 μg/ml of chloramphenicol, it was replicated in minimal medium containing 500 μg/ml of m-fluorophenylalanine to obtain any strains resistant to chloramphenicol and ,resistant to m-fluorophenylalanine. Some of these strains had a plasmid group smaller than pAR-1. Among them, the most miniaturized plasmid was named pAR-112 and the strain carrying pAR-112 was named AJ 12183 (FERM-P 7946). pAR-112 has a restriction enzyme map shown in FIG. 2.

(9) Productivity of phenylalanine, tyrosine and tryptophan with each transformant:

Using pAR-1 and pAR-112 described above, the m-fluorophenylalanine resistant strain Brevibacterium lactofermentum AJ 12184, and the m-fluorophenylalanine and 5-fluorotryptophan doubly resistant strain- which require tyrosine, Brevibacterium lactofermentum M247 were transformed respectively by the method described in (4) and the transformants were selected using chloramphenicol resistance as an index. The thus obtained AJ 12185 (FERM-BP 916 and FERM-P 7945), AJ12184 harboring pAR-1, AJ 12251 (FERM-P 8414 and FERM-BP 918), M247 harboring pAR-112, AJ 12036, AJ 12181, AJ 12182 (FERM-BP 917 and FERM-P 7974) as well as AJ 12183 described above were cultured. The productivity of phenylalanine, tyrosine and tryptophan were examined. The results shown in Table 2 were obtained.

Cultivation was performed by inoculating a specimen strain on 20 ml of aromatic amino acid producing medium described in (7) which was charged in 500 ml of a shoulder-equipped flask and shaken at 30° C for 72 hours. After cultivation, if L-tyrosine was precipitated, 2 ml of a 6N potassium hydroxide solution were added to dissolve the L-tyrosine. The solution was centrifuged and L-phenylalanine, L-tyrosine and L-tryptophan in the supernatant were quantitatively determined by liquid chromatography or a bio-assay method using *Leaconostoc mesentoroides* ATCC 8042.

TABLE 2

| Strain | Amount of L-Phenylalanine, L-Tyrosine and L-Tryptophan Accumulated by Transformants | | |
|---|---|---|---|
| | Amount of L-Phenylalanine Accumulated | Amount of L-Tyrosine Accumulated | Amount of L-Tryptophan Accumulated |
| *Brevibacterium lactofermentum* AJ 12036 | 0 g/dl | 0 g/dl | 0 g/dl |
| *Brevibacterium lactofermentum* AJ 12181 (AJ 12036/pAR-1) | 0.44 g/dl | 0.49 g/dl | 0 g/dl |
| *Brevibacterium lactofermentum* AJ 12183 (AJ 12036/pAR-112) | 0.50 g/dl | 0.53 g/dl | 0 g/dl |
| *Brevibacterium lactofermentum* AJ 12182 (AJ 12036/pAR-2) (FERM-BP 917) | 0.05 g/dl | 0.08 g/dl | 0 g/dl |
| *Brevibacterium lactofermentum* AJ 12184 | 0.62 g/dl | 0.71 g/dl | 0 g/dl |
| *Brevibacterium lactofermentum* AJ 12185 (AJ 12184/pAR-1) (FERM-BP 916) | 0.89 g/dl | 0.95 g/dl | 0 g/dl |
| *Brevibacterium lactofermentum* M 247 | 0.33 g/dl | 0 g/dl | 0.16 g/dl |
| *Brevibacterium lactofermentum* AJ 12251 (M 247/pAR-112) (FERM-BP 918) | 0.64 g/dl | 0 g/dl | 0.24 g/dl |

In order to obtain AJ 12036, AJ 12184 or M247, it is possible to cure the composite plasmid from the deposited AJ 12182, AJ 12185 or AJ 12251 (FERM-BP 918 and FERM-P 8414) respectively without injury to the host cell. That is, the plasmid is spontaneously expelled from host or may also be removed by a curing operation (Bact. Rev., 36, p. 361–405 (1972)). An example curing operation is as follows AJ 12182, AJ 12185 or AJ 12251 is inoculated on CMG liquid medium. After culturing at 37° C. overnight (high temperature treatment), the culture solution is appropriately diluted. The dilution is spread over CMG agar medium containing chloramphenicol or containing no chloramphenicol followed by culturing at 30° C. for 1 to 3 days. The strain thus isolated as a strain sensitive to chloramphenicol is AJ 12036, AJ 12184 or M247, respectively.

The microorganisms identified above by FERM-P 9745 and FERM-P 7947 were originally deposited on Nov. 17, 1984, and the microorganisms identified above by FERM-P 8414 were originally deposited on Aug. 15, 1985 at the Fermentation Research Institute, Agency of Industrial Sciences and Technology, Ministry of International Trade and Industry (FRI), 1-3, Migashi 1-chome, Yatabe-machi, Tsukuba-gun, Ibaragi-ken 305, Japan.

The microorganism deposits were then converted into deposits under the Budapest Treaty on September 27, 1985, and were accorded the corresponding FERM-BP numbers.

All patents and other publications mentioned in this application are indicative of the level of skill of those skilled in the art to which this invention pertains and are individually incorporated herein by reference in the locations where cited.

What is claimed as new and desired to be secured by Letters Patent of the U.S. is:

1. A Coryneform bacterium which comprises a recombinant DNA molecule constructed by connecting (1) a gene capable of being expressed in a Coryneform bacterial cell and coding for 3-deoxy-D-arabino-heptulonic acid-7-phosphate synthetase with (2) a plasmid vector capable of replicating in a Coryneform bacterial cell, wherein said gene is isolated from *Brevibacterium lactofermentum* AJ 11957.

2. The Coryneform bacterium of claim 1, wherein said bacterium is *Brevibacterium lactofermentum* AJ 12181.

3. The Coryneform bacterium of claim 1, wherein said bacterium is *Brevibacterium lactofermentum* AJ 12183.

4. The Coryneform bacterium of claim 1, wherein said bacterium is *Brevibacterium lactofermentum* AJ 12182.

5. The Coryneform bacterium of claim 1, wherein said bacterium is *Brevibacterium lactofermentum* AJ 12185.

6. The Coryneform bacterium of claim 1, wherein said bacterium is *Brevibacterium lactofermentum* AJ 12251.

7. The Coryneform bacterium of claim 1, wherein said bacterium is prepared from a host bacterial strain selected from the group consisting of:
   *Brevibacterium divaricatum* ATCC 14020
   *Brevibacterium saccarolyticum* ATCC 14066
   *Brevibacterium immariophilum* ATCC 14068
   *Brevibacterium lactofermentum* ATCC 13869
   *Brevibacterium roseum* ATCC 13825
   *Brevibacterium flavum* ATCC 13826
   *Brevibacterium thiocenitalis* ATCC 19240
   *Corynebacterium acetoacidophilum* ATCC 13870
   *Corynebacterium acetoclutamicum* ATC 15806
   *Corynebacterium callunae* ATCC 15991
   *Corynebacterium clutamicum* ATCC 13032, 13060
   *Corynebacterium lilium* ATCC 15990
   *Corynebacterium melassecola* ATCC 17965
   *Corynebacterium ammoniaphilum* ATCC 15354
and mutants thereof.

8. The Coryneform bacterium of claim 1, wherein said plasmid vector is selected from the group consisting of pAM 330, pHM 1519, pAJ 655, pAJ 611, pAJ 1844, pCG 1, pCG 2, pCG 4, and pCG 11.

9. The Coryneform bacterium of claim 1, wherein said recombinant DNA molecule is contained in a plasmid vector having all of the identifying characteristics of plasmid pAR-2.

10. The Coryneform bacterium of claim 1, wherein said recombinant DNA molecule is contained in a plasmid vector having all of the identifying characteristics of plasmid pAR-1.

11. The Coryneform bacterium of claim 1, wherein said recombinant DNA molecule is contained in a plasmid vector having all of the identifying characteristics of plasmid pAR-112.

12. A process for producing an aromatic amino acid which comprises culturing a Coryneform bacterium carrying a recombinant DNA molecule constructed by connecting (1) a gene capable of being expressed in a Coryneform bacterial cell and coding for 3-deoxy-D-arabino-heptulonic acid-7-phosphate synthetase with (2) a plasmid vector capable of replication in a Coryneform bacterial cell, wherein said gene is obtained from *Brevibacterium lactofermentum* AJ 11957.

13. The process of claim 12, wherein said recombinant DNA molecule is contained in a plasmid vector having all of the identifying characteristics of plasmid pAR-2.

14. The process of claim 12, wherein said recombinant DNA molecule is contained in a plasmid vector having all of the identifying characteristics of plasmid pAR-1.

15. The process of claim 12, wherein said recombinant DNA molecule is contained in a plasmid vector having all of the identifying characteristics of plasmid pAR-112.

* * * * *